(12) United States Patent
Li

(10) Patent No.: US 7,884,195 B2
(45) Date of Patent: Feb. 8, 2011

(54) METHOD OF EXTRACTING GINSENGNOSIDE RG$_2$M, PHARMACEUTICAL COMPOSITION INCLUDING GINSENGNOSIDE RG$_2$, AND USES THEREOF

(75) Inventor: Long Yun Li, Dong 2 Hong tong, Hong Qi Street, Chao Yang suburb, Changchun (CN) 130-021

(73) Assignees: Long Yun Li, Changchun (CN); Boong-Kung Ko, Seoul (KR)

( * ) Notice: Subject to any disclaimer, the term of this patent is extended or adjusted under 35 U.S.C. 154(b) by 92 days.

(21) Appl. No.: 11/912,804

(22) PCT Filed: Apr. 26, 2005

(86) PCT No.: PCT/KR2005/001204

§ 371 (c)(1),
(2), (4) Date: Oct. 26, 2007

(87) PCT Pub. No.: WO2006/115307

PCT Pub. Date: Nov. 2, 2006

(65) Prior Publication Data

US 2008/0227760 A1 Sep. 18, 2008

(51) Int. Cl.
*C07J 75/00* (2006.01)
(52) U.S. Cl. .......................................... 536/5
(58) Field of Classification Search ................. None
See application file for complete search history.

(56) References Cited

U.S. PATENT DOCUMENTS

| 3,418,311 | A | * | 12/1968 | Sakai et al. | ........... | 536/123 |
| 6,083,932 | A | | 7/2000 | Pang et al. | | |
| 7,438,935 | B2 | * | 10/2008 | Wei et al. | ........... | 424/728 |
| 2004/0247703 | A1 | | 12/2004 | Rhim et al. | | |
| 2005/0031711 | A1 | * | 2/2005 | Park | ........... | 424/728 |

FOREIGN PATENT DOCUMENTS

| CN | 1309969 | 8/2001 |
| DE | 28 28 851 | 1/1980 |
| KR | 2002 0084311 | 11/2002 |
| KR | 2003 0049984 | 6/2003 |
| KR | 2005 0018226 | 2/2005 |
| WO | 00 04912 | 2/2000 |
| WO | 00 37481 | 6/2000 |
| WO | 01 15717 | 3/2001 |

OTHER PUBLICATIONS

MIT "7.6. Two-Solvent Recrystallization Guide", published Jan. 2004, also available at http://ocw.mit.edu/NR/rdonlyres/Chemistry/5-301January--IAP-2004/DDE9861E-3411-4EBD-8210-512B41F785C6/0/8_6_recrystallization.pdf; last viewed Feb. 4, 2010.*
Ma, T. C. et al., "Effect of 20(S)-Ginsenoside-Rg$_2$ and Cyproheptadine on Two-way Active Avoidance Learning and Memory in Rats" In; Arzneimittel Forschung Drug Research, vol. 43 (II), No. 10, pp. 1049-1052, (1993).
Kaku, T. et al., "Isolation and Characterization of Ginsenoside-Rg$_2$, 20R-Prosapogenin, 20S-Prosapogenin and Delta 20-Prosapogenin. Chemical studies on saponins of Panax ginseng C. A. Meyer, Third report" In; Arzneimittelforschung, vol. 30, No. 6, pp. 936-943, (1980).
Kudo, Kenzo et al., "Properties of ginseng saponin inhibition of catecholamine secretion in bovine adrenal chromaffin cells", European Journal of Pharmacology, Elsevier, vol. 341, No. 2-3, pp. 139-144, (1998).
Tachikawa, Eiichi et al., "Effects of ginseng saponins on responses induced by various receptor stimuli", European Journal of Pharmacology, Elsevier, vol. 369, No. 1, pp. 23-32, (1999).
Qun Fang et al. "Micelle-mediated extraction and preconcentration of ginsenosides from Chinese herbal medicine." Journal of Chromatography A, vol. 904, XP004221275, Dec. 2000, pp. 47-55.

* cited by examiner

*Primary Examiner*—Shaojia Anna Jiang
*Assistant Examiner*—Bahar Schmidtmann
(74) *Attorney, Agent, or Firm*—Oblon, Spivak. McClelland, Maier & Neustadt, L.L.P.

(57) ABSTRACT

The present invention provides a method of extracting ginsenoside Rg$_2$, which is applied to mass production. The method of the present invention employs gradient salting-out instead of conventional silica gel chromatography, and therefore enables convenient performance and mass production of ginsenoside Rg$_2$. Provided are also a pharmaceutical composition comprising ginsenoside Rg$_2$ as an active ingredient, and prophylactic and therapeutic agents for preventing and treating dementia, depression, peripheral circulation disorder and related diseases, utilizing the pharmaceutical composition.

8 Claims, 6 Drawing Sheets

METHOD OF EXTRACTING GINSENGNOSIDE RG₂M, PHARMACEUTICAL COMPOSITION INCLUDING GINSENGNOSIDE RG₂, AND USES THEREOF

CROSS-REFERENCE TO RELATED APPLICATIONS

This application is a 371 of PCT/KR05/01204 filed Apr. 26, 2005.

BACKGROUND OF THE INVENTION

1. Field of the Invention

The present invention relates to a method of extracting ginsenoside $Rg_2$, a pharmaceutical composition comprising ginsenoside $Rg_2$ as an active ingredient, and prophylactic and therapeutic agents for preventing and treating dementia, depression, peripheral circulation disorder, and related diseases, utilizing the same.

2. Description of the Related Art

Ginseng contains various ginsenosides (ginseng saponins) and there are around 30 kinds of ginsenosides which have been known hitherto. Among these, ginsenoside $Rg_2$ is a substance belonging to protopanaxatriol glycoside which was isolated and named a long time ago.

It is known through previous research and study that, in the course of red ginseng processing, a glycosidic bond at the C-20 position of ginsenoside $Rg_2$ is readily susceptible to hydrolysis and at the same time, hydroxyl radicals lead to anti-equilibrium, i.e., breakdown of an equilibrium state, thereby forming a ginsenoside isomer C-20(S) or C-20(R). In addition, it is generally published that red ginseng contains mixed-type ginsenoside $Rg_2$ C-20(RS) in a substantially higher content than fresh ginseng or white ginseng.

Meanwhile, since medical use of such ginsenoside $Rg_2$ is as yet unknown, extracting and separating $Rg_2$ has been conventionally carried out, on a laboratory-scale, by extracting ginseng total saponin (GTS) with an organic solvent, and separating ginsenoside $Rg_2$ via silica gel column chromatography or high performance liquid chromatography (HPLC).

Firstly, a silica gel column chromatography process refers to a method involving adsorbing the ginseng total saponin extracts on a silica gel chromatography column, and separating ginsenoside $Rg_2$ therefrom using the organic solvent, in which chloroform, methyl alcohol, ethyl acetate and water are mixed in a predetermined ratio, as a washing agent.

In this connection, the separation method utilizing the above-mentioned silica gel column chromatography mainly suffers from disadvantages such as trace amounts of substance of interest separated from the column, very slow separation speed, a need for an additional separation process due to use of a large quantity of harmful organic solvents, and being unsuitable for large scale production due to high production costs, low yield and unsafety.

Whereas, high performance liquid chromatography (HPLC) enables separation of high-purity ginsenoside $Rg_2$, but presents problems such as high equipment and operation costs and increased production costs associated with use of a large quantity of expensive organic solvents such as methyl alcohol or acetonitrile. Consequently, conventional methods of separating ginsenoside $Rg_2$ are not suitable for mass production of $Rg_2$, thus making it expensive and difficult to enter practical commercial products.

That is, a process suitable for industrial-scale production is preferred to satisfy requirements such as simple and convenient manipulation and processes, easy practical application, high yield and purity, and harmlessness and safety to humans. In spite of such circumstances, research into such a desired process is insignificant.

Meanwhile, there are few published studies and investigations into medicinal usage of ginsenoside $Rg_2$ and application thereof. Even though the present inventors have proposed medical use of ginsenoside $Rg_2$, in Chinese Patent No. ZL01102117.9, entitled "Application of ginsenoside $Rg_2$ in preparation of a therapeutic drug for cardio- and cerebrovascular diseases (CCVD), use of this therapeutic drug is restricted only to treatment of cardio- and cerebrovascular diseases such as myocardial ischemia, cerebral ischemia and shock diseases. As such, there is a need in the art for more advanced and improved research into new medical uses of ginsenoside $Rg_2$.

SUMMARY OF THE INVENTION

Therefore, the present invention has been made in view of the above problems, and it is an object of the present invention to provide a novel method of extracting ginsenoside $Rg_2$, suitable for industrial-scale production.

It is another object of the present invention to provide a pharmaceutical composition comprising ginsenoside $Rg_2$.

It is a further object of the present invention to provide a therapeutic agent comprising ginsenoside $Rg_2$, for preventing or treating dementia, depression, peripheral circulation disorder and related diseases.

In accordance with an aspect of the present invention, the above and other objects can be accomplished by the provision of a method of extracting ginsenoside $Rg_2$ from a raw material of *Araliaceae panax*, comprising:

subjecting the raw material to hot water extraction and concentration to obtain concentrates, adding a lower alcohol to the concentrates to precipitate and remove foreign materials;

decolorizing the remaining supernant and recovering the lower alcohol;

adding a salting-out agent to a saturation concentration so as to obtain precipitates and re-dissolving the precipitates in water, followed by gradient salting-out to obtain differential precipitates corresponding to different concentrations of the salting-out agent;

analyzing to divide the precipitates into ginsenoside $Rg_2$-enriched fractions and ginsenoside $Rg_2$ non-enriched fractions;

destaining and decolorizing the ginsenoside $Rg_2$-enriched fractions with a destaining agent, followed by concentration to obtain concentrates; and adding the lower alcohol to re-crystallize the resulting concentrates, thereby obtaining ginsenoside $Rg_2$.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
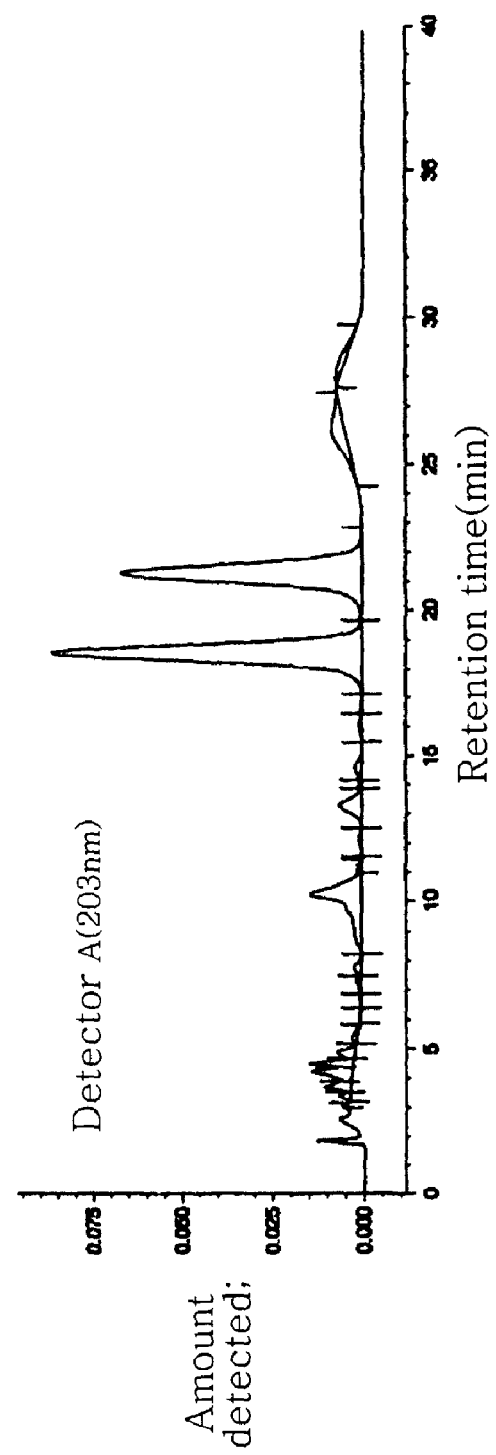
FIG. 1 is a graph showing HPLC analysis results of a crude product of ginsenoside $Rg_2$, isolated from ginseng leaves (*Panax ginseng*)

Hereinafter, the present invention will be described in more detail.

As already known, ginsenoside $Rg_2$ has a molecular formula of $C_{42}H_{72}O_{13}$ and a molecular weight of 784. Structural formula I of ginsenoside $Rg_2$ is as shown below:

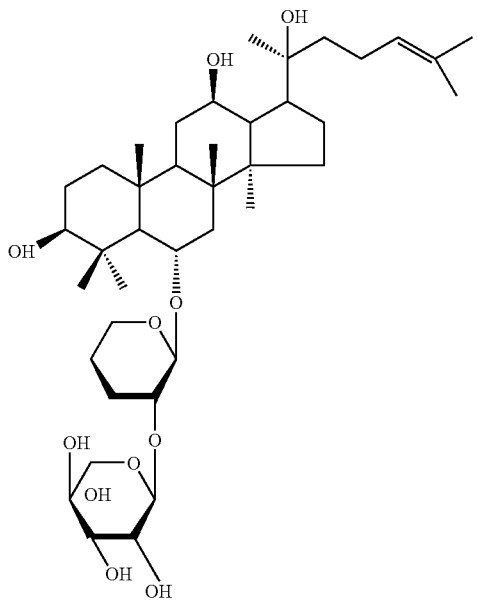

The present invention relating to extraction of ginsenoside $Rg_2$ represented by structural formula 1 employs gradient salting-out, instead of conventional silica gel column chromatography, and thereby can be simply and conveniently performed and is suited for mass production of ginsenoside $Rg_2$. As the salting-out agent which can be utilized in the present invention, mention may be made of sodium chloride, calcium chloride, sodium sulfate, sodium sulfite, ammonium sulfate and any other non-toxic inorganic salts or any combination thereof. The salting-out agent exhibits low-toxicity, is inexpensive, is easily available, and is recoverable thereby being easily re-utilizable.

In addition, the method of the present invention enables acquisition of high-purity ginsenoside $Rg_2$, even with use of relatively inexpensive lower alcohols instead of conventional expensive organic solvents, and also enables obtaining of other ginseng total saponin (GTS) other than $Rg_2$, in the course of gradient salting-out.

Ginsenoside $Rg_2$, which is sought to be extracted in the present invention, can be extracted from raw materials of *Araliaceae panax* plants as described above, and the method preferentially adopted for the raw materials includes the following steps:

a. Raw materials from *Araliaceae panax* plants are added to a 16-fold excess of water and are heat-extracted for 3 hours, repeatedly 3 times. Herein, the raw materials of *Araliaceae panax* include leaves, roots and berries of *Panax ginseng* and American ginseng (*Panax quinquefolius* Linn.);

b. The extracts obtained in step a are concentrated and mixed with a 3 to 4-fold excess of a lower alcohol. Herein, the lower alcohol is selected from the group consisting of methanol, ethanol, isopropyl alcohol, amyl alcohol and any combination thereof;

c. The resulting mixture is stirred to precipitate foreign materials and filtered to obtain a supernant. The supernant is decolorized and alcohol used as the solvent is recovered;

d. A salting-out agent is added to the solution from which the solvent was removed, to a saturation concentration, followed by precipitation for 8 hours, thereby obtaining precipitates. The thus-obtained precipitates are re-dissolved in a 20-fold excess of water and are subjected to gradient salting-out while adding the salting-out agent again, thereby separating and harvesting differential precipitates formed corresponding to different concentrations of the salting-out agent. Herein, the salting-out agent is selected from the group consisting of sodium chloride, calcium chloride, sodium sulfate, sodium sulfite, ammonium sulfate, other non-toxic inorganic salts and any combination thereof;

e. The precipitates, obtained from different concentrations of the salting-out agent by gradient salting-out, are subjected to thin layer chromatography analysis to separately collect ginsenoside $Rg_2$-enriched fractions and ginsenoside $Rg_2$ non-enriched fractions, respectively;

f. The ginsenoside $Rg_2$-enriched fractions are isolated and destained/decolorized using a destaining agent, followed by re-concentration. As the destaining agent, anion or cation exchange resins, adsorbent resins, fillers and the like may be employed. Upon using the ion exchange resin, precipitates of ginsenoside $Rg_2$-enriched fractions are dissolved in a 10-fold excess of 95% ethanol and filtered. The resulting filtrates are diluted with an equal volume of distilled water and then destained. Where the adsorbent resin is used as the salting-out agent, precipitates of ginsenoside $Rg_2$-enriched fractions are dissolved in a 20-fold excess of water and passed through the adsorbent resin to remove inorganic materials. This is followed by destaining through 50% ethanol wash;

g. An alcohol such as ethanol or methanol is added to the destained and concentrated ginsenoside $Rg_2$ solution, thereby obtaining crude products of ginsenoside $Rg_2$, precipitating from a point of higher than 50% concentration;

h. The crude products of ginsenoside $Rg_2$ are recrystallized under different alcohol concentrations on the basis of solubility difference, thereby obtaining respective isomers of high-purity ginsenoside $Rg_2$. For example, the crude products of ginsenoside $Rg_2$ are first dissolved in 70% alcohol and allowed to stand for 12 hours at room temperature, thereby precipitating isomeric C-20(R) ginsenoside $Rg_2$. The alcohol concentration of the resulting supernatant is adjusted to 80%. This is followed by recrystallization at 4° C. for 24 hours to precipitate crystals. The crystals are added to 90% alcohol and heated to 80° C. so as to dissolve crystals, followed by standing at 10° C. for 24 hours to precipitate mixed-type C-20(SR) ginsenoside $Rg_2$. The resulting supernant is allowed to stand for 12 hours at −20° C., thereby precipitating isomeric C-20(S) ginsenoside $Rg_2$.

As such, the extraction method in accordance with the present invention requires no special equipment, is easily performed, provides high purity and yield, is harmless and safe to humans, and therefore is suitable for industrial-scale production. In addition, the method of the present invention does not affect recovery of other ginseng total saponin (GTS).

Further, the present invention provides a pharmaceutical composition comprising ginsenoside $Rg_2$ extracted by the above-mentioned extraction method. The pharmaceutical composition comprises 1 to 99% by weight of R- or S-isomer ginsenoside $Rg_2$, or a mixture thereof, and 99 to 1% by weight of a pharmaceutically acceptable carrier and adjuvant. More preferably, the pharmaceutical composition comprises more than 50% by weight of ginsenoside $Rg_2$ as an active ingredient.

The pharmaceutically acceptable carrier and adjuvant may be selected from the group consisting of starch, talcum powder, sugar, flavoring substance, dextrin, medical-grade ethanol, polyethylene glycol, propylene glycol, vegetable oil, gelatin and Tween 80 (Polyoxyethylene Sorbitan Monooleate) and other surfactants.

More specifically, the pharmaceutical composition may further comprise a diluting agent and excipient such as water; fillers such as starch and sucrose; binding agents such as cellulose derivatives, alginate, gelatin and polyvinyl pyrrolidone; a wetting agent such as glycerin; disintegrating agents such as agar, calcium carbonate, and sodium hydrogen carbonate; an absorption promoter such as a quaternary ammonium salt; a surfactant such as hexadecanol; adsorbent carriers such as kaolin and crude clay; lubricating agents such as talcum powder, calcium stearate, magnesium and polyethylene. Besides these, other adjuvants such as flavoring agents and sweetening agents may be added as constituent substances.

Further, in accordance with the present invention, the pharmaceutical composition containing ginsenoside $Rg_2$ can be formulated into injectable preparations, capsules, pills, tablets, nebula, oral solutions, patches, suppositories, microcapsules and micro balls, all of which are conventionally used in Chinese and Western medicines.

More specifically, the pharmaceutical composition may be applied to injectable preparations such as powder for injection and injectable solution; tablets such as dragee, chewing tablets and film-coated tablets; capsules such as normal and micro capsules; nebula; suppositories such as anal and vaginal suppositories; buccal mucous membrane patches; chewable pills; syrups and other oral solutions.

Meanwhile, it was confirmed through the following experimental examples that the pharmaceutical composition prepared in accordance with the method of the present invention had therapeutic action on dementia, including presenile dementia, typically Alzheimer and vascular dementia, typically multiple infarct dementia (MID) and also had anti-depressant activity and improved effects of excitation center and peripheral circulation.

By medical definition, dementia belongs to a category of disorders stemming from deterioration of mental and nervous functions. In other words, dementia is also called intellectual (perception, memory, speculation, inference and judgment, emotion, etc.) inability due to brain organic mental disorders, and is known to be caused by degeneration or death of nerve cells.

However, use of anti-dementia drugs known hitherto provided slight improvement in symptoms via enhanced action of a neurotransmitter, i.e., acetylcholine, but failed to prevent underlying pathogenic causes, i.e., degeneration and death of nerve cells. Consequently, as acetylcholinergic neurons are damaged and glutaminergic neurons are also damaged, at the early stage of dementia, enhancement of acetylcholine activity has at most transient effects on patients in the early stage of dementia development.

On the other hand, glutamic acid is the most abundant neurotransmitter in the brain, and thus it is expected that if a glutamic acid activator is developed, therapeutic effects upon dementia thereof will be superior to those of an acetylcholine activator. However, similar to the acetylcholine activator, the glutamic acid activator also plays a role in enhancing interaction between remaining nerve cells after occurrence of nerve cell damage, rather than preventing damage of nerve cells. Therefore, if the glutamic acid activator is administered in an excess amount, this may result in damage of nerve cells and thus cannot serve as a substantial treatment for dementia, a primary cause of which is cell death.

Recent study further demonstrates that damage of nerve cells induced by insoluble beta-amyloid is a primary cause of intellectual disability. Therefore, the key point for treatment of dementia is to enhance action of neurotransmitters and at the same time to prevent degeneration or death of nerve cells.

Meanwhile, depression is a clinically frequent psychotic disease, and also manifests mental disorder-causing general emotional symptoms. At present, etiology of depression is not exactly known, but decreased synthesis of the neurotransmitters belonging to intracerebral monoamines is known to be involved in development of depression.

The known anti-depressant imipramine increases concentrations of noradrenalin (NA) and 5-hydroxytryptamine (5-HT) in synaptic clefts. Some species of monoamine oxidase inhibitors also increase concentrations of intracerebral monoamine neurotransmitters.

Currently, an animal model of depression is established on the basis of a monoamine neurotransmitter theory. Therefore, control of intracerebral monoamine neurotransmitters has become a major focus in treatment of psychotic diseases or mental disorders.

In compliance with such circumstances, when ginsenoside $Rg_2$, obtained by the extraction method of the present invention, was applied to the following animal experiments, ginsenoside $Rg_2$ exerted excellent therapeutic action on dementia, exhibited significantly improved action on memory disorders caused by both insoluble beta-amyloid proteins and multiple cerebral infarction, controlled apoptosis of cerebral nerve cells, inhibited expression of apoptosis-related genes/proteins, and prevented loss and death of nerve cell bodies while simultaneously inhibiting damage of correlated nerve cells caused by glutamic acid and excitatory amino acids.

Further, it was also found through various other animal experiments that ginsenoside $Rg_2$ in accordance with the present invention remarkably increased the concentration of intracerebral monoamine neurotransmitters, thereby exerting pronounced anti-depressant effects, and remarkably reduced sleeping time exerted by pentobarbital sodium, thus possessing cerebral cortex-stimulating action.

EXAMPLES

Now, the present invention will be described in more detail with reference to the following examples. These examples are provided only for illustrating the present invention and should not be construed as limiting the scope and spirit of the present invention.

Example 1

Extraction of Ginsenoside $Rg_2$ from Ginseng Leaves (*Panax ginseng*)

First, 100 kg of ginseng leaves were added to a 16-fold amount of water and boiled for 3 hours. This procedure was repeated 3 times. The resulting liquids were combined and filtered through a filter. The filtrates were concentrated to approximately 100 kg in a concentrator. The resulting concentrates were added to 3-fold excess of 95% ethanol, stirred to precipitate foreign materials and re-filtered to remove precipitated foreign materials. The thus-separated supernant was decolorized using activated charcoal and the ethanol solvent used was then recovered.

The supernant, from which ethanol was removed, was dissolved in a 10-fold excess of water, and the resulting solution was saturated with high-purity ammonium sulfate, followed by precipitation for 8 hours. The thus-obtained precipitates were re-dissolved in a 20-fold excess of water and subjected to gradient salting-out with continuous addition of high-purity ammonium sulfate. At 5%, 10%, 15%, 20% and 30% concentrations of ammonium sulfate in the solution, the resulting respective precipitates were collected.

The precipitates collected according to different concentrations of the salting-out agent were aliquoted and subjected to thin layer chromatography analysis, thereby being divided into ginsenoside $Rg_2$-enriched fractions (precipitates at 15% and 20% concentrations of ammonium sulfate) and other ginsenoside $Rg_2$ non-enriched fractions (precipitates at 5%, 10% and 30% concentrations of ammonium sulfate). Precipitates of ginsenoside $Rg_2$-enriched fractions were isolated and dissolved in a 10-fold excess of 95% ethanol and filtered to obtain filtrates. The filtrates thus obtained were diluted 1-fold with distilled water, followed by destaining and decolorizing via an ion exchange resin. The thus-treated filtrates were concentrated to 1,000 ml.

The concentrates were added again to 95% ethanol to obtain crude products of ginsenoside $Rg_2$—beginning to precipitate from the point at which the ethanol concentration in the solution rose above 50%. Purity of precipitated crude products of ginsenoside $Rg_2$ was measured at 203 nm, via high performance liquid chromatography (HPLC). The results are shown in Table 1 and FIG. 1, respectively.

TABLE 1

| Pk# | Retention time (min) | Area (peak value × peak time duration) | Area % | Theoretical plate |
|---|---|---|---|---|
| 1 | 3.034 | 2955 | 0.035 | 0.00 |
| 2 | 3.377 | 32346 | 0.380 | 1583.78 |
| 3 | 3.673 | 99726 | 1.171 | 1431.46 |
| 4 | 4.211 | 191479 | 2.248 | 1458.20 |
| 5 | 4.482 | 125818 | 1.477 | 3877.20 |
| 6 | 4.860 | 80246 | 0.942 | 1459.10 |
| 7 | 5.355 | 30188 | 0.354 | 1848.53 |
| 8 | 6.085 | 4651 | 0.055 | 0.00 |
| 9 | 6.666 | 4788 | 0.056 | 3306.51 |
| 10 | 7.293 | 23324 | 0.274 | 1438.15 |
| 11 | 7.739 | 41530 | 0.488 | 2408.69 |
| 12 | 10.216 | 668782 | 7.851 | 2542.60 |
| 13 | 11.133 | 7692 | 0.090 | 10971.31 |
| 14 | 12.139 | 17798 | 0.209 | 5089.94 |
| 15 | 13.260 | 193484 | 2.271 | 3968.55 |
| 16 | 14.080 | 11252 | 0.132 | 0.00 |
| 17 | 14.595 | 61696 | 0.724 | 3420.54 |
| 18 | 16.030 | 21353 | 0.251 | 4112.83 |
| 19 | 16.701 | 12897 | 0.151 | 2347.50 |
| 20 | 18.561 | 3437480 | 40.353 | 5085.97 |
| 21 | 21.269 | 3021268 | 35.467 | 5180.98 |
| 22 | 26.232 | 316288 | 3.713 | 0.00 |
| 23 | 27.902 | 111465 | 1.309 | 0.00 |
| Total | | 8518505 | 100.000 | |

As can be seen from the data of Table 1 and FIG. 1, purity of ginsenoside $Rg_2$ crude products, as measured in terms of the sum of Area % for peaks 20 and 21, with a retention time ranging from 18 to 22 min, was 75.81%.

In addition, the thus-obtained ginsenoside $Rg_2$ crude products were dissolved in 70% ethanol and allowed to stand at room temperature for 12 hours, thereby precipitating isomeric C-20(R) ginsenoside $Rg_2$ in the form of crystals. Then, the ethanol concentration of the resulting supernatant was adjusted to 80%, followed by recrystallization at 4° C. for 24 hours to precipitate crystals. The crystals were added to 90% ethanol, heated to 80° C., and left at 10° C. for 24 hours, thereby precipitating mixed-type C-20(SR) ginsenoside $Rg_2$ in the form of crystals. Then, the resulting supernant was allowed to stand at −20° C. for 12 hours, thereby precipitating isomeric C-20(S) ginsenoside $Rg_2$ as crystals.

The respective different isomers of ginsenoside $Rg_2$ crystals were finally purified, filtered under reduced pressure and spontaneously dried in the air at room temperature for 24 hours, thereby sequentially obtaining 20 g of isomeric C-20 (S) ginsenoside $Rg_2$, 238 g of mixed-type C-20(SR) ginsenoside $Rg_2$ and 30 g of isomeric C-20(R) ginsenoside $Rg_2$. Additionally, 2100 g of ginseng saponin was obtained in $Rg_2$ non-enriched fractions.

When the respective isomers of ginsenoside $Rg_2$ thus obtained were determined by a gravimetric method (expressed as % mass of extracted and separated ginsenoside $Rg_2$ for 100 kg of ginseng leaves used as raw materials), yield of C-20(SR) ginsenoside $Rg_2$ was 0.24%, yield of C-20(S) ginsenoside $Rg_2$ was 0.02%, and yield of C-20(R) ginsenoside $Rg_2$ was 0.03%.

In addition, purity of the respective different isomers of ginsenoside $Rg_2$ was measured at 203 nm, via high performance liquid chromatography (HPLC). The results are shown in Tables 2 through 4 and FIGS. 2 through 4, respectively.

TABLE 2

| Pk# | Retention time (min) | Area (peak value × peak time duration) | Area % | Theoretical plate |
|---|---|---|---|---|
| 1 | 3.361 | 2492 | 0.014 | 2492.06 |
| 2 | 3.663 | 53477 | 0.306 | 2161.39 |
| 3 | 4.177 | 40047 | 0.230 | 0.00 |
| 4 | 4.486 | 2446 | 0.014 | 8005.15 |
| 5 | 4.980 | 1684 | 0.010 | 2585.79 |
| 6 | 6.693 | 4707 | 0.027 | 0.00 |
| 7 | 7.298 | 8494 | 0.049 | 0.00 |
| 8 | 7.682 | 4710 | 0.027 | 1918.52 |
| 9 | 7.893 | 1724 | 0.010 | 0.00 |
| 10 | 8.800 | 4037 | 0.023 | 285.71 |
| 11 | 8.869 | 2534 | 0.015 | 0.00 |
| 12 | 9.080 | 2565 | 0.015 | 1393.54 |
| 13 | 9.207 | 2181 | 0.012 | 221.50 |
| 14 | 9.318 | 1710 | 0.010 | 1199.20 |
| 15 | 9.703 | 10485 | 0.060 | 394.82 |
| 16 | 10.164 | 65134 | 0.373 | 2495.55 |
| 17 | 10.967 | 23 | 0.000 | 735389.56 |
| 18 | 11.033 | 615 | 0.004 | 0.00 |
| 19 | 11.091 | 2472 | 0.014 | 4875.31 |
| 20 | 12.096 | 10381 | 0.059 | 864.65 |

TABLE 2-continued

| Pk# | Retention time (min) | Area (peak value × peak time duration) | Area % | Theoretical plate |
|---|---|---|---|---|
| 21 | 13.250 | 115126 | 0.660 | 3274.46 |
| 22 | 14.556 | 99695 | 0.571 | 3218.61 |
| 23 | 16.016 | 42054 | 0.241 | 0.00 |
| 24 | 16.622 | 42576 | 0.244 | 115.97 |
| 25 | 18.446 | 8261910 | 47.349 | 4799.02 |
| 26 | 21.116 | 8629243 | 49.454 | 4757.97 |
| 27 | 23.079 | 72 | 0.000 | 0.00 |
| 28 | 23.233 | 20 | 0.000 | 3136816.00 |
| 29 | 24.355 | 9418 | 0.054 | 0.00 |
| 30 | 25.953 | 9923 | 0.057 | 0.00 |
| 31 | 28.515 | 17110 | 0.098 | 0.00 |
| Total | | 17449064 | 100.000 | |

Figure 2:
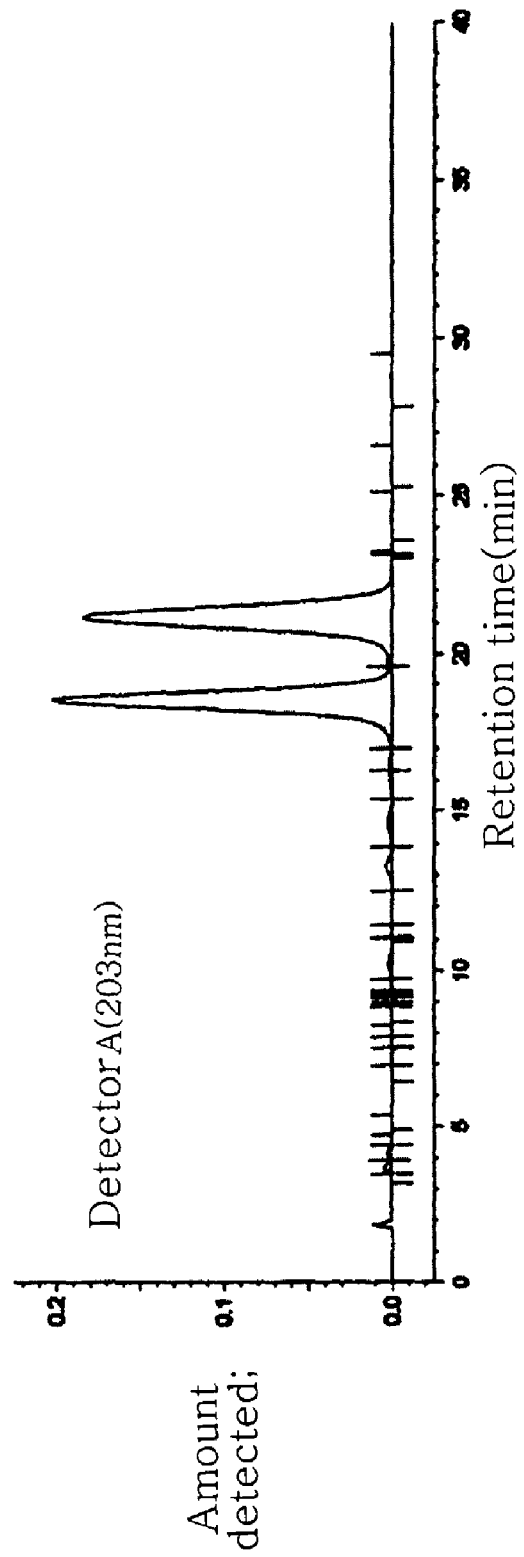
FIG. 2 is a graph showing HPLC analysis results of mixed-type ginsenoside $Rg_2$, isolated from ginseng leaves (*Panax ginseng*)

As can be seen from the data of Table 2 and FIG. 2, purity of mixed-type C-20(SR) ginsenoside $Rg_2$, as measured in terms of the sum of Area % for peaks 25 and 26, with a retention time ranging from 18 to 22 min, was 96.80%.

TABLE 3

| Pk# | Retention time (min) | Area (peak value × peak time duration) | Area % | Theoretical plate |
|---|---|---|---|---|
| 1 | 3.037 | 121 | 0.001 | 0.00 |
| 2 | 3.220 | 92 | 0.001 | 9538.11 |
| 3 | 3.433 | 454 | 0.003 | 1972.74 |
| 4 | 3.670 | 32302 | 0.224 | 2289.08 |
| 5 | 4.154 | 7107 | 0.049 | 1141.86 |
| 6 | 4.497 | 2088 | 0.014 | 5509.86 |
| 7 | 4.903 | 7983 | 0.055 | 1492.92 |
| 8 | 6.230 | 7394 | 0.051 | 2003.41 |
| 9 | 6.664 | 9846 | 0.068 | 1263.64 |
| 10 | 7.673 | 27398 | 0.190 | 54.15 |
| 11 | 7.940 | 15722 | 0.109 | 0.00 |
| 12 | 10.129 | 166788 | 1.157 | 122.33 |
| 13 | 10.483 | 59464 | 0.412 | 186.53 |
| 14 | 11.063 | 87894 | 0.610 | 383.29 |
| 15 | 12.005 | 265257 | 1.840 | 1998.89 |
| 16 | 13.094 | 1403530 | 9.735 | 3804.62 |
| 17 | 14.433 | 663230 | 4.600 | 2047.64 |
| 18 | 15.781 | 342779 | 2.378 | 1902.34 |
| 19 | 16.483 | 231848 | 1.608 | 1212.25 |
| 20 | 18.230 | 10305761 | 71.484 | 5057.40 |
| 21 | 20.988 | 543020 | 3.767 | 3841.79 |
| 22 | 24.228 | 190829 | 1.324 | 3466.42 |
| 23 | 25.656 | 45929 | 0.319 | 0.00 |
| Total | | 14416834 | 100.000 | |

Figure 3:
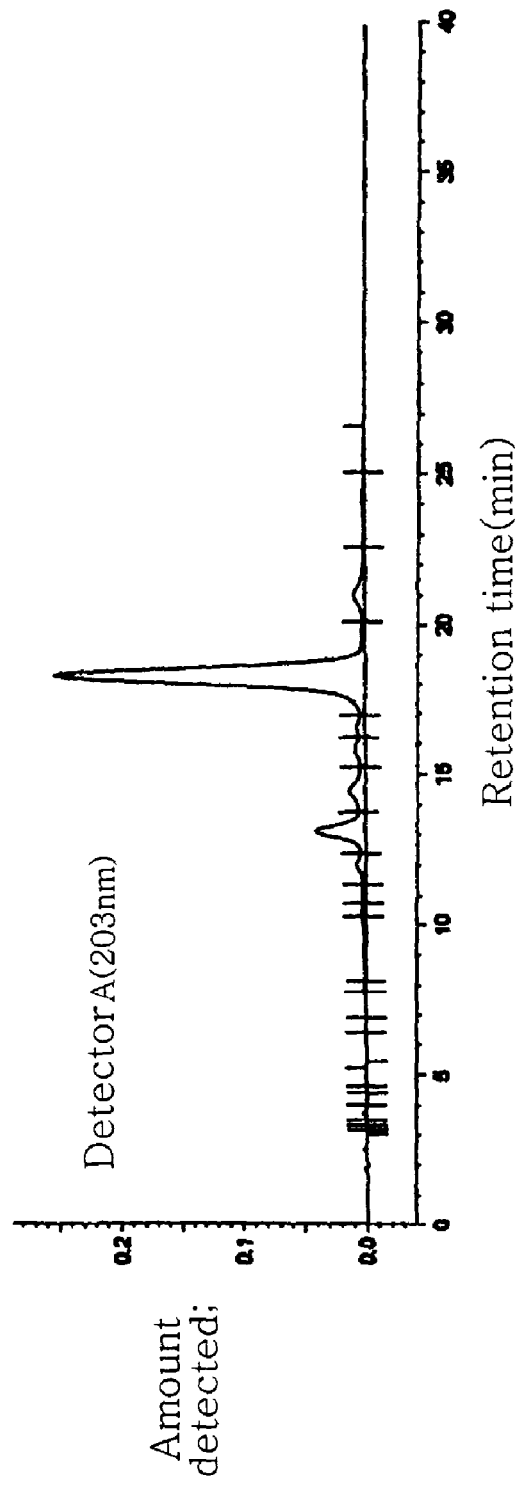
FIG. 3 is a graph showing HPLC analysis results of S-type ginsenoside $Rg_2$, isolated from ginseng leaves (*Panax ginseng*)

As can be seen from the data of Table 3 and FIG. 3, purity of isomeric C-20(S) ginsenoside $Rg_2$, as measured in terms of the sum of Area % for peaks 20 and 21, with a retention time ranging from 18 to 22 min, was 75.25%.

TABLE 4

| Pk# | Retention time (min) | Area (peak value × peak time duration) | Area % | Theoretical plate |
|---|---|---|---|---|
| 1 | 3.222 | 99 | 0.003 | 8425.45 |
| 2 | 3.413 | 124 | 0.003 | 9811.11 |
| 3 | 3.671 | 25369 | 0.683 | 2331.91 |
| 4 | 4.145 | 354 | 0.010 | 7352.22 |
| 5 | 4.479 | 5032 | 0.135 | 7809.87 |
| 6 | 6.664 | 1740 | 0.047 | 5713.31 |
| 7 | 7.633 | 1231 | 0.033 | 7793.26 |
| 8 | 14.429 | 2982 | 0.080 | 0.00 |
| 9 | 15.294 | 822 | 0.022 | 0.00 |
| 10 | 18.361 | 382028 | 10.281 | 5601.45 |
| 11 | 20.987 | 3261726 | 87.776 | 5554.10 |

TABLE 4-continued

| Pk# | Retention time (min) | Area (peak value × peak time duration) | Area % | Theoretical plate |
|---|---|---|---|---|
| 12 | 25.710 | 30713 | 0.827 | 0.00 |
| 13 | 26.805 | 3746 | 0.101 | 0.00 |
| Total | | 3715968. | 100.000 | |

Figure 4:
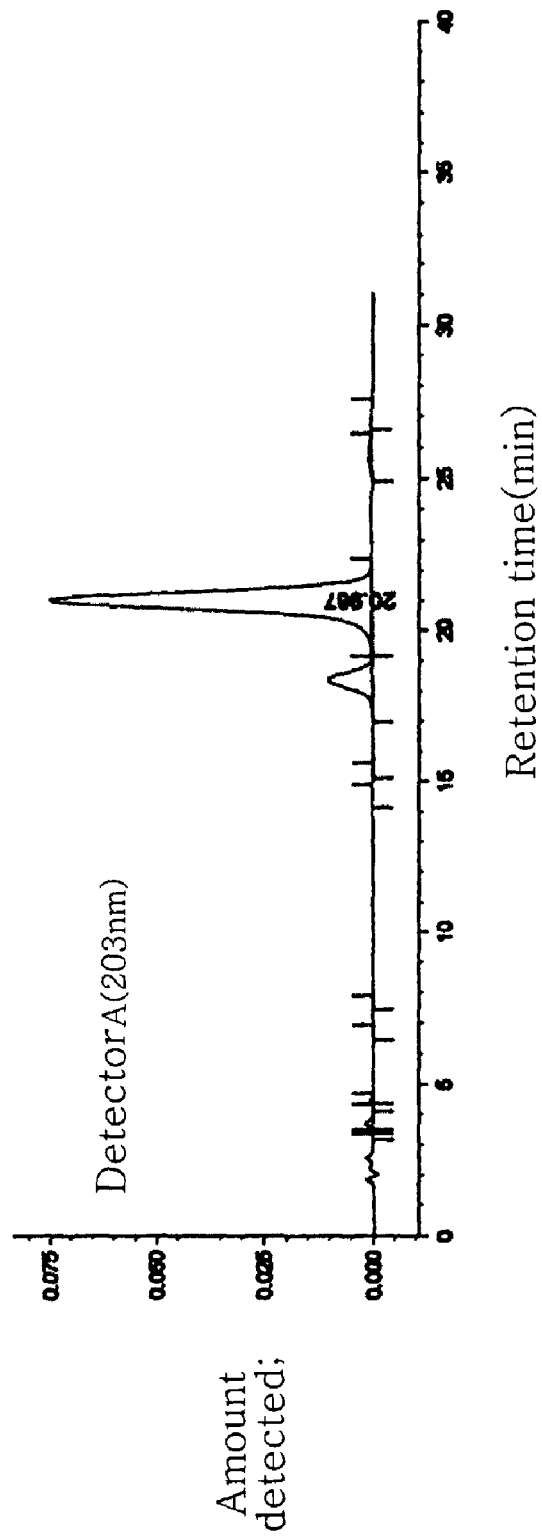
FIG. 4 is a graph showing HPLC analysis results of R-type ginsenoside $Rg_2$, isolated from ginseng leaves (*Panax ginseng*)

As can be seen from the data of Table 4 and FIG. 4, purity of isomeric C-20(R) ginsenoside $Rg_2$, as measured in terms of the sum of Area % for peaks 20 and 21, with a retention time ranging from 18 to 22 min, was 98.05%.

Example 2

Extraction of Ginsenoside $Rg_2$ from American Ginseng Leaves (*Panax quinquefolius* Linn.)

Figure 5:
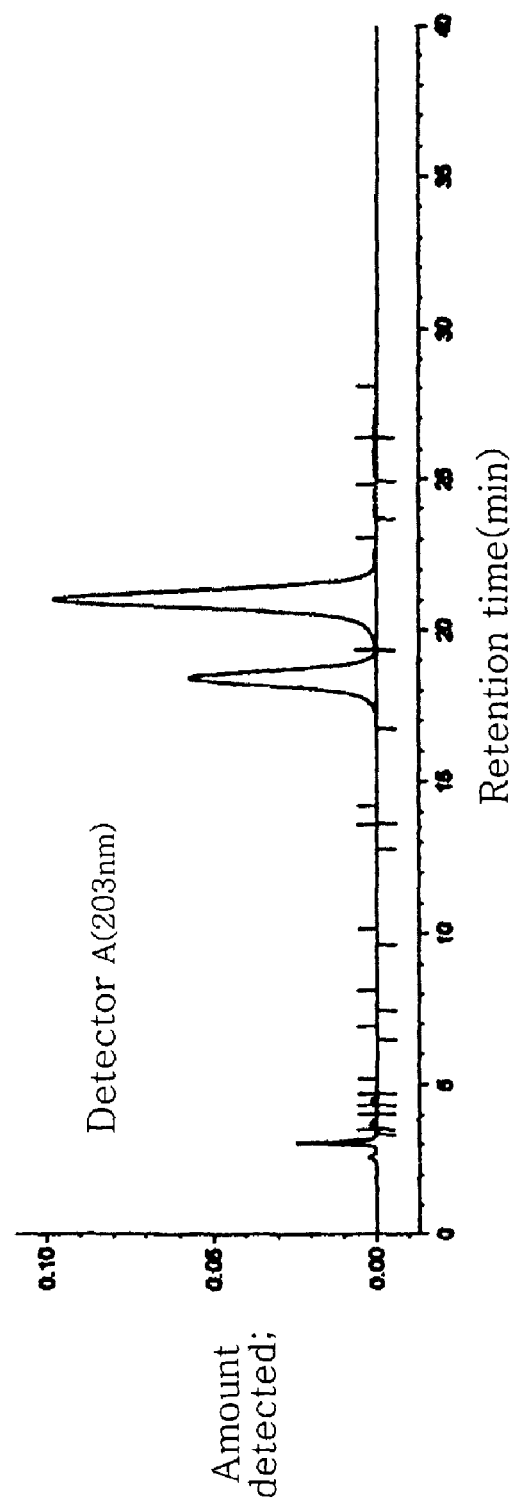
FIG. 5 is a graph showing HPLC analysis results of mixed-type ginsenoside $Rg_2$, isolated from leaves of American ginseng (*Panax quinquefolius* Linn.)

75 g of mixed-type C-20(SR) ginsenoside $Rg_2$ was obtained using 50 kg of American ginseng leaves (*Panax quinquefolius* Linn.), according to the same procedure as in Example 1. In the same manner as in Example 1, yield and purity of C-20(SR) ginsenoside $Rg_2$ were determined. Yield was 0.15%. Purity was 97.41%, as can be seen from the data of Table 5 and FIG. 5

TABLE 5

| Pk# | Retention time (min) | Area (peak value × peak time duration) | Area % | Theoretical plate |
|---|---|---|---|---|
| 1 | 3.049 | 66979 | 1.007 | 0.00 |
| 2 | 3.422 | 477 | 0.007 | 10207.29 |
| 3 | 3.677 | 22110 | 0.332 | 2462.35 |
| 4 | 4.173 | 904 | 0.014 | 8237.63 |
| 5 | 4.494 | 14288 | 0.215 | 7087.08 |
| 6 | 4.912 | 894 | 0.013 | 0.00 |
| 7 | 6.687 | 953 | 0.014 | 4984.06 |
| 8 | 7.672 | 1661 | 0.025 | 7191.44 |
| 9 | 9.888 | 1653 | 0.025 | 10264.50 |
| 10 | 13.156 | 3551 | 0.053 | 0.00 |
| 11 | 13.903 | 1023 | 0.015 | 10016.99 |
| 12 | 18.398 | 2191765 | 32.948 | 5575.19 |
| 13 | 21.035 | 4288045 | 64.462 | 5553.44 |
| 14 | 24.184 | 5421 | 0.082 | 0.00 |
| 15 | 25.672 | 29789 | 0.448 | 0.00 |
| 16 | 26.906 | 22585 | 0.340 | 0.00 |
| Total | | 6652099 | 100.000 | |

Example 3

Extraction of Ginsenoside $Rg_2$ from Ginseng Berry (*Panax ginseng*)

Figure 6:
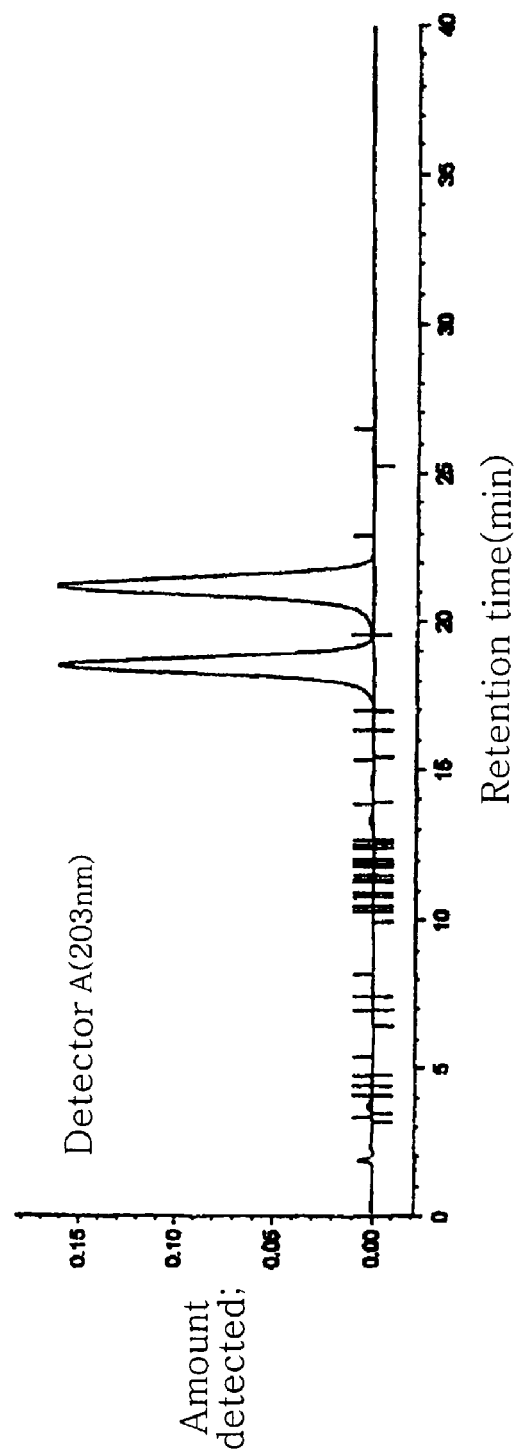
FIG. 6 is a graph showing HPLC analysis results of mixed-type ginsenoside $Rg_2$, isolated from ginseng berries (*Panax ginseng*).

50 kg of ginseng berry was added to small quantities of water. Fruit flesh was crushed to remove seeds and concentrated to prepare a syrup. In the same manner as in Example 1, 125 g of mixed-type C-20(SR) ginsenoside $Rg_2$ was obtained from the syrup. In the same manner as in Example 1, yield and purity of C-20(SR) ginsenoside $Rg_2$ were determined. Yield was 0.25%. Purity was 98.55%, as can be seen from the data of Table 6 and FIG. 6.

TABLE 6

| Pk# | Retention time (min) | Area (peak value × peak time duration) | Area % | Theoretical plate |
|---|---|---|---|---|
| 1 | 3.201 | 122 | 0.001 | 12340.68 |
| 2 | 3.666 | 28434 | 0.204 | 2308.68 |
| 3 | 4.212 | 2874 | 0.021 | 2468.14 |
| 4 | 4.481 | 4354 | 0.031 | 6820.24 |
| 5 | 5.017 | 2284 | 0.016 | 0.00 |
| 6 | 6.689 | 1429 | 0.010 | 0.00 |
| 7 | 7.233 | 921 | 0.007 | 0.00 |
| 8 | 7.668 | 6803 | 0.049 | 5732.65 |
| 9 | 10.232 | 749 | 0.005 | 0.00 |
| 10 | 10.313 | 509 | 0.004 | 8705.97 |
| 11 | 10.472 | 592 | 0.004 | 13533.43 |
| 12 | 10.860 | 98 | 0.001 | 123277.41 |
| 13 | 11.109 | 1636 | 0.012 | 20884.91 |
| 14 | 11.300 | 157 | 0.001 | 0.00 |
| 15 | 11.431 | 103 | 0.001 | 0.00 |
| 16 | 11.780 | 286 | 0.002 | 27707.96 |
| 17 | 11.873 | 283 | 0.002 | 0.00 |
| 18 | 12.000 | 622 | 0.004 | 0.00 |
| 19 | 12.131 | 1791 | 0.013 | 0.00 |
| 20 | 12.467 | 77 | 0.001 | 238945.98 |
| 21 | 12.620 | 77 | 0.001 | 287686.34 |
| 22 | 13.271 | 47850 | 0.343 | 4493.61 |
| 23 | 14.570 | 47079 | 0.337 | 0.00 |
| 24 | 16.009 | 15535 | 0.111 | 0.00 |
| 25 | 16.678 | 16021 | 0.115 | 0.00 |
| 26 | 18.488 | 6388832 | 45.758 | 5169.40 |
| 27 | 21.150 | 7385339 | 52.895 | 5126.25 |
| 28 | 26.081 | 7433 | 0.053 | 0.00 |
| Total | | 13962290 | 100.000 | |

Hereinafter, experiments on therapeutic effects of dementia, anti-depressant action and improving effects of excitation center and peripheral circulation were conducted, using ginsenoside $Rg_2$ extracted in Examples 1 through 3.

Experimental Example 1

Therapeutic Effects of Ginsenoside $Rg_2$ on Beta-Amyloid ($A\beta_{1-40}$) Dementia This experiment was carried out employing an Alzheimer Dementia (AD) model. 70 rats were divided into 7 groups consisting of 10 rats each and were anesthetized with chloral hydrate. Except for a placebo group, the remaining 6 groups were rendered dementia models by injecting 4 μg of beta-amyloid ($A\beta_{1-40}$) and 1 μg of Ibotenic acid (IBA) into the hippocampus CA1 region of each rat. The placebo group was infused with an equal amount of physiological saline, instead of beta-amyloid and Ibotenic acid (IBA).

The above-mentioned dementia model groups were subdivided into a control group to which physiological saline was administered, four experimental groups to which ginsenoside $Rg_2$ was administered and a comparative group to which a medical dementia therapeutic agent, nimodipine was administered. Each group received the corresponding respective reagents via intravenous injection for 7 days, once a day, according to the dosages set forth in Table 7 below. Herein, reagents, which are administered to experimental groups, are isomeric C-20(S) ginsenoside $Rg_2$ and C-20(R) ginsenoside $Rg_2$, and mixed-type C-20(SR) ginsenoside $Rg_2$ (in the following Tables, referred to as S, R and SR, respectively).

On day 6 of respective reagent administration, animals were subjected to a Y-shaped electronic maze test. Learning-memory ability of rats was determined according to the following method. Firstly, the order of learning is taken as the number of stimulus times necessary for 9 to 10-time successive and exact response of rats. After 24 hours, the stimulus times necessary for 9 to 10-time successive and exact response of rats were recorded again as the order of memory. Based on the recordings thus obtained, a t-test was made between respective groups. The results are shown in Table 7 below.

TABLE 7

| Groups | Reagents | Amount administered (mg·kg$^{-1}$) | Order of Learning | Order of Memory |
|---|---|---|---|---|
| Placebo | — | — | 10.8 ± 4.73 | 3.10 ± 3.12 |
| Control | Saline | 10 | 27.9 ± 3.35$^{\triangle\triangle}$ | 26.0 ± 4.69$^{\triangle\triangle}$ |
| Experimental | $Rg_2$(S) | 7.50 | 15.8 ± 6.08** | 13.6 ± 6.59** |
| | $Rg_2$(R) | 7.50 | 14.8 ± 5.88** | 12.6 ± 7.89** |
| | $Rg_2$(SR) | 7.50 | 16.8 ± 7.45** | 14.6 ± 9.58** |
| | $Rg_2$(SR) | 15.0 | 12.4 ± 6.87** | 3.30 ± 2.79** |
| Comparative | Nimodipine | 0.05 | 8.60 ± 4.58** | 4.10 ± 4.80** |

(Compared with the placebo group; $^{\triangle\triangle}P < 0.01$; compared with the dementia model groups: **$P < 0.01$)

As can be seen from Table 7, upon examining learning-memory ability of rats to which beta-amyloid ($A\beta_{1-40}$) and Ibotenic acid (IBA) were intracerebrally administered, experimental groups to which respective different structures of ginsenoside $Rg_2$ were administered exhibited significantly improved learning-memory ability, as compared to the control group exhibiting symptoms of typical beta-amyloid dementia.

In addition, 24 hours after examination of learning-memory ability, the front and rear of the injected site of the hippocampus CA1 region were successively sliced and subjected to Niss1 staining, HE staining, and chemical examination of immune tissues and in situ cell death, thereby observing morphological changes of hippocampus neuron cell zones, necrosis, degree of cell loss, rate of cell death, and degree of expression of Bax/Bcl-2 and C-fos genes. The results are shown in Tables 8 through 11.

TABLE 8

| Groups | Reagents | Amount administered (mg·kg$^{-1}$) | Length of nerve cell body loss (μm) |
|---|---|---|---|
| Control | Saline | 10 | 648.16 ± 61.52 |
| Experimental | $Rg_2$(S) | 7.50 | 303.21 ± 59.00** |
| | $Rg_2$(R) | 7.50 | 283.23 ± 69.60** |
| | $Rg_2$(SR) | 7.50 | 343.23 ± 59.60** |
| | $Rg_2$(SR) | 15.0 | 275.33 ± 56.59** |
| Comparative | Nimodipine | 0.05 | 259.14 ± 60.36** |

(Note: Compared with the control group: **$P < 0.01$)

As can be seen from Table 8, Niss1 staining revealed that intracerebral injection of $A\beta_{1-40}$ and IBA caused a wide range loss of nerve cell bodies, as demonstrated by the control group, but obvious inhibitory effects against loss of the nerve cell bodies were observed in experimental groups to which the respective isomers of ginsenoside $Rg_2$ were administered.

TABLE 9

| Groups | Reagents | Amount administered (mg·kg$^{-1}$) | Rate of nerve cell death |
|---|---|---|---|
| Control | Saline | 10 | 50.67 ± 6.15 |
| Experimental | $Rg_2$(S) | 7.50 | 24.80 ± 5.73* |
| | $Rg_2$(R) | 7.50 | 23.83 ± 4.62* |

TABLE 9-continued

| Groups | Reagents | Amount administered (mg · kg$^{-1}$) | Rate of nerve cell death |
|---|---|---|---|
| | Rg$_2$(SR) | 7.50 | 25.00 ± 5.73* |
| | Rg$_2$(SR) | 15.0 | 23.33 ± 3.98* |
| Comparative | Nimodipine | 0.05 | 19.83 ± 2.93* |

(Note: Compared with the control: *P < 0.05)

As can be seen from Table 9, examination of in situ cell death (apoptosis) by TUNEL (Terminal deoxynucleotidyl Transferase Biotin-dUTP Nick End Labeling) staining revealed that injection of Aβ$_{1-40}$ and IBA into the hippocampus induced death of nerve cells, as demonstrated by the control group, but death of nerve cells was remarkably reduced in experimental groups to which the respective isomers of ginsenoside Rg$_2$ were administered.

TABLE 10

| Groups | Reagents | Amount administered (mg · kg$^{-1}$) | Expression Intensity of bax | | | | Expression Intensity of bcl-2 | | | |
|---|---|---|---|---|---|---|---|---|---|---|
| | | | − | + | ++ | +++ | − | + | ++ | +++ |
| Placebo | — | — | 1 | 8 | 1 | 0 | 0 | 1 | 9 | 0 |
| Control | Saline | 10 | 0 | 1 | 3 | 6$^{ΔΔ}$ | 0 | 8 | 2 | 0$^{ΔΔ}$ |
| Experimental | Rg$_2$(S) | 7.50 | 0 | 7 | 3 | 0** | 0 | 3 | 6 | 1** |
| | Rg$_2$(R) | 7.50 | 0 | 6 | 3 | 1** | 0 | 2 | 8 | 0** |
| | Rg$_2$(SR) | 7.50 | 0 | 7 | 2 | 1** | 0 | 2 | 7 | 1** |
| | Rg$_2$(SR) | 15.0 | 0 | 8 | 2 | 0** | 0 | 1 | 9 | 0** |
| Comparative | Nimodipine | 0.05 | 0 | 7 | 3 | 0** | 0 | 5 | 4 | 1** |

(Note: Compared with the placebo group: $^{ΔΔ}$P < 0.01; compared with the control: *P < 0.05, **P < 0.01)

TABLE 11

| Groups | Reagents | Amount administered (mg · kg$^{-1}$) | Expression Intensity of C-fos | | | |
|---|---|---|---|---|---|---|
| | | | − | + | ++ | +++ |
| Placebo | — | — | 6 | 4 | 0 | 0 |
| Control | Saline | 10 | 1 | 4 | 5 | 0$^{ΔΔ}$ |
| Experimental | Rg$_2$(S) | 7.50 | 0 | 0 | 6 | 4** |
| | Rg$_2$(R) | 7.50 | 0 | 1 | 6 | 3** |
| | Rg$_2$(SR) | 7.50 | 0 | 0 | 6 | 4** |
| | Rg$_2$(SR) | 15.0 | 0 | 1 | 4 | 5** |
| Comparative | Nimodipine | 0.05 | 0 | 3 | 4 | 3* |

(Note: Compared with the placebo group: $^{ΔΔ}$P < 0.01; compared with the control: *P < 0.05, **P < 0.01)

As can be seen from Tables 10 and 11, upon examining expression of apoptosis-promoting regulator (Bax), apoptosis-inhibiting regulator (Bcl-2) and transcriptional regulator (C-fos), the control group with beta-amyloid (Aβ$_{1-40}$) dementia symptoms exhibited increased expression of Bax and decreased expression of Bcl-2. Whereas, experimental groups to which the respective isomers of ginsenoside Rg$_2$ were administered exhibited decreased expression of Bax and enhanced expression of Bcl-2 and C-fos. These results demonstrate that the respective isomers of ginsenoside Rg$_2$ have regulatory action on expression of abnormal Bax and Bcl-2 genes.

In addition, results of HE staining showed that the placebo group exhibited less damage to hippocampal neurons, slight damage around sites to which an injection needle penetrated, small quantities of gliocyte infiltration, but intactness and no loss of pyramidal cell zones.

On the other hand, the control group manifesting beta-amyloid dementia symptoms exhibited large quantities of gliocyte infiltration, significant loss of hippocampal neurons. The region of cell death extended a great distance from CA1 near an injection point, and thus a very long pyramidal-granular cell zone was observed to be lost. Upon examination under a high magnification microscope, rupture of the neuronal cell membrane, cellular atrophy, reduction of cell nuclei, and apoptotic bodies were apparently observed.

In contrast, experimental groups, to which the respective isomers of ginsenoside Rg$_2$ were administered, did not exhibit local infiltration of gliocytes, damage to pyramidal cell zones and granular cell zones, diminishing of cells and loss of cell zones. Upon examination under a high magnification microscope, cell membranes were intact, apoptotic bodies were very rare or nearly non-existent in a region more distant than CA1 and pathological changes were also observed to be very slight.

In conclusion, for dementia models showing AD behavior and pathological changes caused by injection of beta-amyloid (Aβ$_{1-40}$) and Ibotenic acid (IBA) mixtures into the hippocampus region of the rat brain, the respective isomers of ginsenoside Rg$_2$ can significantly improve learning and memory ability in AD rats, as with an anti-dementia drug, nimodipine, prevent loss of nerve cell bodies, increase expression of C-fos and bcl-2 in the brain, but inhibit expression of bax. Therefore, nerve cell bodies are protected and death thereof is prevented.

Experimental Example 2

Therapeutic Effects of Ginsenoside Rg$_2$ on Multiple Infarct Dementia

This experiment was carried out employing a multiple infarct dementia (MID) model. 56 rats were divided into 7 groups consisting of 8 rats each and were anesthetized with 10% chloral hydrate. Except for a placebo group, the remaining 6 groups were established as dementia models by injecting 0.13 ml/100 g of a composite thrombosis-inducing agent into the carotid artery of each rat, restoring anatomical structures thereof and suturing skins along layers. The placebo group was injected with an equal amount of physiological saline, instead of the composite thrombosis-inducing agent.

The above dementia model groups were subdivided into a control group to which physiological saline was administered, four experimental groups to which ginsenoside $Rg_2$ was administered and a comparative group to which a medical dementia therapeutic agent, nimodipine was administered. Each group received the corresponding respective reagents via intravenous injection for 7 days, once a day, according to dosages set forth in Table 12 below. Herein, reagents, which are administered to experimental groups, are isomeric C-20(S) ginsenoside $Rg_2$ and C-20(R) ginsenoside $Rg_2$, and mixed-type C-20(SR) ginsenoside $Rg_2$ (in the following experiments, referred to as S, R and SR, respectively).

On day 6 of respective reagent administration, learning-memory ability of animals was determined according to the same manner as in Experimental Example 1. The results are shown in Table 12 below.

TABLE 12

| Groups | Reagents | Amount administered (mg · kg$^{-1}$) | Order of Learning | Order of Memory |
|---|---|---|---|---|
| Placebo | — | — | 2.1 ± 3.18 | 2.1 ± 3.18 |
| Control | Saline | 10 | 14 ± 11.63$^{ΔΔ}$ | 7.3 ± 9.52$^{ΔΔ}$ |
| Experimental | $Rg_2$(S) | 5.0 | 1.3 ± 5.58* | 0.7 ± 1.41* |
|  | $Rg_2$(R) | 5.0 | 3.3 ± 4.58* | 0.6 ± 3.24* |
|  | $Rg_2$(SR) | 5.0 | 3.7 ± 5.10* | 0.7 ± 1.41* |
|  | $Rg_2$(SR) | 10.0 | 4.6 ± 4.16* | 0.1 ± 0.32* |
| Comparative | Nimodipine | 0.05 | 2.5 ± 3.70* | 0.0 ± 0.0* |

(Compared with the placebo group; $^{Δ}p < 0.01$; compared with the control group: $*P < 0.05$)

As can be seen from Table 12, upon examining and determining learning-memory ability of rats, the control group with typical multiple infarct dementia (MID) symptoms exhibited increased order of learning and memory, but experimental groups to which respective structures of ginsenoside $Rg_2$ were administered exhibited significantly decreased learning and memory orders. These results demonstrate that the respective isomers of ginsenoside $Rg_2$ have significantly improved therapeutic effects on multiple infarct dementia.

In addition, 24 hours after determination of learning-memory ability, the heads of animals were dissected, and a 2×5 mm incision was made in the bregma, at front and rear sides, respectively, and fixed with 4% paraformaldehyde, covered with paraffin and sectioned into sections having a thickness of 7 μm using a paraffin microtome. The sections were subjected to Nissl staining, and chemical tests were carried out on glutamate (Glu), apoptosis promoting regulator (Bax), an apoptosis inducer Caspase-3 and a protease Calpain II-positive neurons in a CPU region in rats of immunized groups. The results are shown in Tables 13 and 14.

TABLE 13

| Groups | Reagents | Amount administered (mg · kg$^{-1}$) | Number of Glu-positive cells | Number of Bax-positive cells |
|---|---|---|---|---|
| Placebo | — | — | 5.5 ± 1.4 | 0.025 ± 0.05 |
| Control | Saline | 10 | 16.2 ± 3.43$^{ΔΔ}$ | 10.2 ± 1.48$^{ΔΔ}$ |
| Experimental | $Rg_2$(S) | 5.0 | 6.5 ± 3.65** | 4.0 ± 1.87** |
|  | $Rg_2$(R) | 5.0 | 5.7 ± 2.63** | 3.4 ± 1.62** |
|  | $Rg_2$(SR) | 5.0 | 6.1 ± 2.65** | 4.0 ± 1.87** |
|  | $Rg_2$(SR) | 10.0 | 6.3 ± 3.46** | 1.7 ± 0.97** |
| Comparative | Nimodipine | 0.05 | 11.8 ± 3.89* | 3.2 ± 2.47** |

(Compared with the placebo group; $^{ΔΔ}p < 0.01$; compared with the control group: $*P < 0.05$, $**P < 0.01$)

TABLE 14

| Groups | Reagents | Amount administered (mg · kg$^{-1}$) | Number of Caspase-3 positive cells | Number of Calpain II-positive cells |
|---|---|---|---|---|
| Placebo | — | — | 1.5 ± 2.58 | 1.0 ± 0.91 |
| Control | Saline | 10 | 33.0 ± 13.01$^{ΔΔ}$ | 13.9 ± 3.14$^{ΔΔ}$ |
| Experimental | $Rg_2$(S) | 5.0 | 0.4 ± 1.12** | 4.0 ± 1.07** |
|  | $Rg_2$(R) | 5.0 | 0.2 ± 2.12** | 3.0 ± 2.07** |
|  | $Rg_2$(SR) | 5.0 | 0.2 ± 0.34** | 3.5 ± 1.09** |
|  | $Rg_2$(SR) | 10.0 | 0.7 ± 1.16** | 3.0 ± 1.73** |
| Comparative | Nimodipine | 0.05 | 2.3 ± 2.72** | 3.9 ± 0.67** |

(Compared with the placebo group; $^{ΔΔ}p < 0.01$; compared with the control group: $**P < 0.01$)

From chemical examinations of immunized groups, as shown in Tables 13 and 14, it was confirmed that rats of experimental groups to which respective different structures of ginsenoside $Rg_2$ were administered exhibited significant reduction in expression of Glu, Bax, Caspase-3, Calpain II-positive neurons in the CPU region, as compared with the control group having typical MID dementia symptoms, demonstrating that respective structures of ginsenoside $Rg_2$ have regulatory action on expression of the above abnormal genes.

In conclusion, for dementia models with MID behavior and pathological changes caused by injection of the composite thrombosis-inducing agent to rats, it was confirmed that the respective isomers of ginsenoside $Rg_2$ can significantly improve learning and memory ability in MID rats, similar to another anti-dementia drugs, nimodipine, and such action was correlated with declined expression of Glu, Calpain II, Caspase-3 and Bax involved in protein death.

Experimental Example 3

Effects of Ginsenoside $Rg_2$ on MTT Metabolism after Damage of PC12 Cells

100 μl/well of PC12 culture having a cell density of 10$^5$ cells/mL was inoculated into a 96-well plate and PC12 cells were allowed to adhere to walls of the plate. Wells were divided into 6 groups to which 6 wells were assigned each.

A serum-free medium was added to a non-treatment group, 1 mmol/L of a serum-free medium containing glutamic acid and an equal volume (1 mmol/L) of 20% 1,2-polyethylene glycol were added to a control group, 1 mmol/L of a serum-free medium containing glutamic acid and 0.1 mmol/L of respective structures of ginsenoside $Rg_2$ were added to experimental groups, and 5 pmol of nimodipine, instead of ginsenoside $Rg_2$, was added to a comparative group. Then, PC12 cells of respective groups were cultured at 37° C. for 20 hours.

20 μl/well of MTT (5 g/L) was added to respective groups and cells were continuously cultured at 37° C. for 4 hours. Then, the original medium was aspirated, and 0.1 ml/well of dimethyl sulfoxide (DMSO) was added to dissolve red granules. Next, optical density (OD) at 490 nm was measured using an enzyme-linked immuno-assay and then a t-test was made between groups. Results are shown in Table 15.

TABLE 15

| Groups | Reagents | Amount administered (mmol/L) | MTT (OD) |
|---|---|---|---|
| Non-treatment | — | — | 0.094 ± 0.016 |
| Control | Polyethylene glycol | 1 | 0.060 ± 0.010$^{\Delta}$ |
| Experimental | $Rg_2(S)$ | 0.1 | 0.087 ± 0.016* |
|  | $Rg_2(R)$ | 0.1 | 0.083 ± 0.016* |
|  | $Rg_2(SR)$ | 0.1 | 0.083 ± 0.015* |
| Comparative | Nimodipine | 5 pmol | 0.086 ± 0.017* |

(Compared with the non-treatment group; $^{\Delta}P < 0.05$; compared with the control group: *P < 0.05)

As can be seen from Table 15, the control group exhibited significantly reduced MTT metabolism, confirming that glutamic acid partially damaged PC12 cells. Whereas, in comparison with the control group, it was confirmed that both experimental and comparative groups, to which respective structures of ginsenoside $Rg_2$ and nimodipine were administered, respectively, exhibited significantly increased MTT metabolism of PC12 cells, thus demonstrating that all of the respective isomeric ginsenoside $Rg_2$ can inhibit damage of PC12 cells affected by glutamic acid.

Experimental Example 4

Therapeutic Effects of Ginsenoside $Rg_2$ on Depression

A general model of depression adopts drug- or stress stimulation, but this experiment adopts ischemia/reperfusion to lower contents of norepinephrine (NE), dopamine (DA) and 5-hydroxytryptamine (5-HT) in brain tissues, thereby establishing a depression model.

48 rats were divided into 6 groups consisting of 8 rats each and were anesthetized with 10% chloral hydrate. Except for a placebo group, the remaining 5 groups were established as depression models as follows. A nylon line was inserted from a left external carotid artery into an internal carotid artery of each rat and a middle cerebral artery (MCA) was occluded. 30 min after blockage of blood flow, the nylon line was removed and reperfusion was allowed, thereby establishing depression models of rats.

Among the above depression models, 10 mg·kg$^{-1}$ of physiological saline was administered to a control group, and respective structures of ginsenoside $Rg_2$ were intravenously injected into experimental groups for 5 consecutive days, once a day, according to dosages set forth in Table 16 below.

After 48 hours of respective reagent administration, learning-memory ability of rats was determined according to the same manner as in Experimental Example 1. The results are shown in Table 16 below.

TABLE 16

| Groups | Reagents | Amount administered (mg·kg$^{-1}$) | Order of Learning | Order of Memory |
|---|---|---|---|---|
| Placebo | — | — | 5.0 ± 1.41 | 3.4 ± 1.19 |
| Control | Saline | 10 | 28.3 ± 2.19$^{\Delta\Delta}$ | 26.0 ± 2.67$^{\Delta\Delta}$ |
| Experimental | $Rg_2(S)$ | 7.50 | 17.5 ± 3.28** | 13.8 ± 2.98** |
|  | $Rg_2(R)$ | 7.50 | 19.0 ± 3.89** | 15.8 ± 3.69** |
|  | $Rg_2(SR)$ | 7.50 | 12.0 ± 2.97** | 8.9 ± 2.42** |
|  | $Rg_2(SR)$ | 15.0 | 10.9 ± 2.42** | 7.9 ± 3.04** |

(Compared with the placebo group; $^{\Delta\Delta}P < 0.01$; compared with the control group: *P < 0.01)

In addition, 6 days after examination of learning-memory ability, heads of rats were dissected to remove the brain which was then homogenized. Contents of cerebral neurotransmitters, such as norepinephrine (NE), dopamine (DA) and 5-hydroxytryptamine (5-HT) were determined, and thereby a t-test was made between respective groups. The results are shown in Table 17 below.

TABLE 17

| Groups | Reagents | Amount administered (mg·kg$^{-1}$) | NE (ng/g) | DA (ng/g) | 5-HT (ng/g) |
|---|---|---|---|---|---|
| Placebo | — | — | 1212.8 ± 49.50 | 321.8 ± 33.0 | 191.1 ± 33.24 |
| Control | Saline | 10 | 783.8 ± 74.25$^{\Delta\Delta}$ | 165.0 ± 24.75$^{\Delta\Delta}$ | 0.12 ± 33.24$^{\Delta\Delta}$ |
| Experimental | $Rg_2(S)$ | 7.50 | 958.0 ± 66.0** | 298.0 ± 33.0* | 106.3 ± 48.17** |
|  | $Rg_2(R)$ | 7.50 | 858.0 ± 66.0** | 198.0 ± 33.0* | 108.0 ± 41.55** |
|  | $Rg_2(SR)$ | 7.50 | 973.5 ± 49.5** | 239.3 ± 41.25** | 116.3 ± 58.17** |
|  | $Rg_2(SR)$ | 15.0 | 1014.8 ± 132.0** | 272.3 ± 24.75** | 157.9 ± 24.93** |

(Compared with the placebo group; $^{\Delta\Delta}P < 0.01$; compared with the control group: *P < 0.05, **P < 0.01)

As can be seen from Tables 16 and 17, the control group exhibited remarkable decreases in learning-memory ability and cerebral NE and DA contents, while all of the experimental groups, to which respective isomers of ginsenoside $Rg_2$ were administered, exhibited remarkable increases in learning/memory ability and cerebral NE, DA and 5-HT contents.

According to the monoamine theory, it can be confirmed that respective isomers of ginsenoside $Rg_2$ have pronounced ameliorating action on depression or diseases resulting from disturbance in stimulation/suppression of central nervous system.

Experimental Example 5

Effects of Ginsenoside $Rg_2$ on Pentobarbital Sodium-Induced Sleeping Time 38 male mice were divided into three groups as set forth in Table 18 below. Mixed-type ginsenoside $Rg_2$ was intravenously administered in an amount of 10 and 20 mg·kg$^{-1}$ to experimental groups, respectively. At the same time, 50 mg·kg$^{-1}$ of pentobarbital sodium was intravenously administered again. Whereas, for the control group, 10 mg·kg$^{-1}$ of 20% 1,2-polyethylene glycol was intravenously administered, instead of ginsenoside $Rg_2$. Using loss of lighting reflex as an indicator, a sleeping time of the mice belonging to the respective groups was recorded and a t-test was made between the respective groups. The results are shown in Table 18.

TABLE 18

| Groups | Reagents | Amount administered (mg · kg$^{-1}$) | Number of animals (n) | Sleeping time (min) |
|---|---|---|---|---|
| Control | Polyethylene glycol | 10.0 | 12 | 17.09 ± 10.41 |
| Experimental | Rg$_2$(SR) | 10.0 | 13 | 9.41 ± 5.91* |
| | Rg$_2$(SR) | 20.0 | 13 | 8.39 ± 6.55* |

(Compared with the control group: *P < 0.05)

In comparison with the control group, as shown in Table 18, all of the experimental groups, to which mixed-type ginsenoside Rg$_2$ was administered, exhibited great reduction in the sleeping time of mice induced by pentobarbital sodium, demonstrating that ginsenoside Rg$_2$ stimulates the central nervous system (CNS).

Experimental Example 6

Therapeutic Effects of Ginsenoside Rg$_2$ on Peripheral Circulation Disorders of Auricle 68 male mice were divided into 6 groups as set forth in Table 19 below and were anesthetized with urethane. Under a microscope, each strand of the venule (V) and arteriole (A) in the auricle was located. A diameter of each blood vessel was measured and state of blood flow was observed and recorded.

For the above groups, a control group was injected with physiological saline, and a comparative group was injected with an injectable preparation containing 0.2 g/mL of red ginseng and Big Blue Lily turf (*Liriope platyphylla* Wang et Tang) mixed extract. For experimental groups, respective structures of ginsenoside Rg$_2$ were intravenously injected according to dosages set forth in Table 19 below. 5 min later, 0.01 mg·kg$^{-1}$ of adrenalin was re-administered. Diameters of blood vessels, state of blow flow and numbers of vascular network intersection points were measured every hour.

Calculating percentage changes in adrenaline based on results thus measured, a t-test between respective groups was carried out. The results are shown in Tables 19, 20 and 21 below.

TABLE 19

| Groups | Reagents | Amount administered (mg · kg$^{-1}$) | Number of animals (n) | Changes in diameter of venous capillary vessel with respect to the time (%) | | | | |
|---|---|---|---|---|---|---|---|---|
| | | | | 1 min | 5 min | 10 min | 15 min | 20 min |
| Control | Saline | 10.0 | 12 | 27.0 ± 14.9 | 27.0 ± 11.52 | 16.7 ± 8.41 | 15.5 ± 7.53 | 11.98 ± 9.89 |
| Comparative | Ginseng-Big Blue Lily Turf | 10.0 × 10$^3$ | 11 | 10.02 ± 12.41** | 6.24 ± 15.43** | −3.93 ± 12.03*** | −5.06 ± 12.54*** | −1.66 ± 11.72** |
| Experimental | Rg$_2$(S) | 10.0 | 11 | 14.91 ± 18.26 | 9.15 ± 10.52** | 5.02 ± 10.30* | 2.25 ± 10.39* | −1.01 ± 10.94* |
| | Rg$_2$(R) | 10.0 | 11 | 15.51 ± 17.26 | 10.15 ± 10.52** | 41.42 ± 11.12** | 3.25 ± 8.39* | −0.81 ± 0.94* |
| | Rg$_2$(SR) | 10.0 | 11 | 13.68 ± 19.51 | 9.42 ± 18.00* | 4.15 ± 13.00* | 2.29 ± 11.72** | −0.77 ± 0.72*** |
| | Rg$_2$(SR) | 20.0 | 12 | 5.24 ± 9.96*** | 6.30 ± 12.78*** | 0.42 ± 12.13*** | −0.89 ± 9.63*** | −1.31 ± 11.42** |

(Compared with the control group: *P < 0.05, P < 0.01, *P < 0.001)

TABLE 20

| Groups | Reagents | Amount administered (mg · kg$^{-1}$) | Number of animals (n) | Changes in diameter of arterial capillary vessel with respect to the time (%) | | | | |
|---|---|---|---|---|---|---|---|---|
| | | | | 1 min | 5 min | 10 min | 15 min | 20 min |
| Control | Saline | 10.0 | 12 | 27.6 ± 22.8 | 19.17 ± 12.5 | 15.02 ± 12.61 | 15.91 ± 14.14 | 9.86 ± 15.28 |
| Comparative | Ginseng-Big Blue Lily Turf | 10.0 × 10$^3$ | 11 | 23.75 ± 20.91 | 12.21 ± 12.66 | 8.09 ± 12.15 | 6.82 ± 12.25 | 5.86 ± 11.03 |
| Experimental | Rg$_2$(S) | 10.0 | 11 | 25.65 ± 19.93 | 8.60 ± 13.48** | 6.75 ± 10.24* | 4.57 ± 7.18* | −2.04 ± 7.05* |
| | Rg$_2$(R) | 10.0 | 11 | 27.65 ± 18.30 | 9.60 ± 12.40** | 7.75 ± 11.24* | 3.57 ± 8.30* | −1.04 ± 6.15* |
| | Rg$_2$(SR) | 10.0 | 11 | 33.74 ± 19.62 | 9.42 ± 18.00* | 7.39 ± 12.04* | 3.57 ± 8.30* | 0.0 ± 0.0** |
| | Rg$_2$(SR) | 20.0 | 12 | 26.65 ± 20.23 | 16.88 ± 14.48 | 6.14 ± 10.73* | 3.17 ± 7.25* | 0.75 ± 3.20** |

(Compared with the control group: *P < 0.05, P < 0.01, *P < 0.001)

TABLE 21

| Group | Reagents | Amount administered (mg · kg$^{-1}$) | Number of animals (n) | Changes in intersection points of peripheral circulation with respect to the time (%) | | | | |
|---|---|---|---|---|---|---|---|---|
| | | | | 1 min | 5 min | 10 min | 15 min | 20 min |
| Control | Saline | 10.0 | 12 | 78.29 ± 22.36 | 47.78 ± 12.58 | 30.12 ± 17.13 | 24.26 ± 17.07 | 22.26 ± 21.06 |
| Comparative | Ginseng-Big | 10.0 × 10$^3$ | 11 | 33.64 ± 19.87*** | 11.11 ± 16.41*** | 6.25 ± 11.85*** | 2.08 ± 7.22*** | 1.04 ± 3.61** |

TABLE 21-continued

| Group | Reagents | Amount administered (mg · kg$^{-1}$) | Number of animals (n) | Changes in intersection points of peripheral circulation with respect to the time (%) | | | | |
|---|---|---|---|---|---|---|---|---|
| | | | | 1 min | 5 min | 10 min | 15 min | 20 min |
| | Blue Lily Turf | | | | | | | |
| Experimental | Rg$_2$(S) | 10.0 | 11 | 33.05 ± 12.02*** | 4.76 ± 7.74*** | 0.13 ± 0.51*** | 0.56 ± 1.24*** | 0.0 ± 0.0** |
| | Rg$_2$(R) | 10.0 | 11 | 31.55 ± 11.32*** | 5.76 ± 9.04*** | 1.13 ± 1.50*** | 1.56 ± 2.24*** | 0.0 ± 0.0** |
| | Rg$_2$(SR) | 10.0 | 11 | 27.79 ± 20.67*** | 4.36 ± 8.32*** | 0.0 ± 0.0*** | 0.0 ± 0.0*** | 0.0 ± 0.0** |
| | Rg$_2$(SR) | 20.0 | 12 | 14.51 ± 16.25*** | 2.83 ± 5.93*** | 1.10 ± 3.69*** | 1.92 ± 9.93*** | 0.0 ± 0.0** |

(Compared with the control group: *P < 0.05, P < 0.01, *P < 0.001)

As can be seen from Tables 19 through 21, experimental groups, to which respective isomers of ginsenoside Rg$_2$ were administered, exhibited significant inhibition against reduction of blood vessel diameter of the arterioles and venules of mouse auricles caused by adrenalin and reduction of the number of vascular network intersection points, as compared with the control group.

Additionally, as compared to the control group to which the preparation containing a mixture of red ginseng and Big Blue Lily turf was injected, the ginsenoside Rg$_2$-administered experimental groups displayed a much less decrease in terms of a degree of reduction in blood vessel diameters and a degree of reduction in the number of vascular network intersection points, with respect to the passage of time. In particular, inhibitory action against reduction in the blood vessel diameter of venules was much stronger than in arterioles.

Experimental Example 7

Effects of Ginsenoside Rg$_2$ on Ear Perfusion of Rabbit 33 white rabbits were divided into 4 groups as set forth in Table 22 below and were anesthetized with pentobarbital sodium. Arteries of the ear roots were stripped and tubes were inserted therein. The remaining blood was washed with a Locke solution and the rabbit ears were dissected, followed by perfusion.

For the above groups, a control group was injected with physiological saline, and a comparative group was injected with an injectable preparation containing 0.2 g/mL of red ginseng and Big Blue Lily turf (Liriope platyphylla Wang et Tang) mixed extract. For experimental groups, mixed-type ginsenoside Rg$_2$ was administered via the tube according to dosages set forth in Table 22 below. Before administration of reagents and at intervals of 3 min after administration, changes in the number of perfusion drops were expressed as a degree of peripheral vasodilation and then t-test between groups was carried out. The results are shown in Table 22 below.

TABLE 22

| Group | Reagents | Amount administered (mg · kg$^{-1}$) | | | Number of drops after administration | | |
|---|---|---|---|---|---|---|---|
| | | | | | 0~3 min | 4~6 min | 7~9 min |
| Control | Saline | 0.675 | 8 | 69.7 ± 14.76 | 2.0 ± 1.51 | −2.9 ± 4.25 | −3.3 ± 4.03 |
| Comparative | Ginseng-Big Blue Lily Turf | 250 | 8 | 63.0 ± 11.9 | 44.0 ± 12.24*** | 24.0 ± 7.80*** | 17.4 ± 8.07*** |
| Experimental | Rg$_2$(S) | 0.63 | 8 | 67.4 ± 18.01 | 16.1 ± 8.84*** | 8.5 ± 4.07*** | 5.0 ± 5.21** |
| | Rg$_2$(R) | 1.25 | 9 | 68.6 ± 16.85 | 14.1 ± 7.04*** | 5.8 ± 6.70** | 1.8 ± 4.92* |

(Compared with the control group: *P < 0.05, P < 0.01, *P < 0.001)

As can be seen from Table 22, experimental groups, to which mixed-type ginsenoside Rg$_2$ was administered, displayed significant increase in the number of perfusion drops after administration of Rg$_2$, as compared to the control group, demonstrating that mixed-type ginsenoside Rg$_2$ has vasodilating action on peripheral vessels.

INDUSTRIAL APPLICABILITY

As disclosed from the foregoing, a method of extracting ginsenoside Rg$_2$ in accordance with the present invention employs gradient salting-out substituting conventional silica gel column chromatography separation, and therefore is suitable for mass production of Rg$_2$ due to easy and convenient operation and manipulation, enables extraction of high-purity finished products even with use of relatively cheap lower alkane alcohol instead of expensive mixed organic solvents, and thereby provides effects such as low production costs, harmlessness, safety and no influence on recovery of other ginseng saponins from the remaining materials.

In addition, the present invention reveals that respective isomers of ginsenoside Rg$_2$ have significantly improved action on memory disorders of animals with dementia caused by insoluble beta-amyloid proteins and multiple cerebral infarction, can control expression of genes or proteins involved in apoptosis/anti-apoptosis of cerebral neurons, prevent loss and death of neurons and inhibit damage of PC12 cells caused by glutamic acid.

In addition, the present invention has confirmed that respective isomers of ginsenoside Rg$_2$ significantly increase concentrations of monoamine neurotransmitters such as intracerebral NE, 5-HT and DA in cerebral blood deficit-reperfusion rats, and ginsenoside Rg$_2$ has distinctive antidepressant action according to a monoamine theory. Additionally, ginsenoside $Rg_2$ significantly reduces pentobarbital sodium-induced sleeping time, demonstrating that ginsenoside $Rg_2$ exerts stimulatory effects upon the cerebral cortex.

Further, the present invention demonstrates that respective isomers of ginsenoside $Rg_2$ have significantly improved effects on peripheral circulation disorders of the mouse auricle and increasing effects of perfusion rate in rabbit ears, representing that ginsenoside $Rg_2$ has vasodilating action on peripheral vessels.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of extracting ginsenoside $Rg_2$ from leaves and berries of *Araliaceae panax* and American ginseng (*Panax quinquefolius* Linn.) plants, comprising:
   subjecting the raw material to hot-water extraction and concentration to obtain concentrates, adding a lower alcohol to the concentrates to precipitate and remove foreign materials;
   decolorizing the remaining supernatant and recovering the lower alcohol;
   adding a salting-out agent to a saturation concentration so as to obtain precipitates and re-dissolving the precipitates in water, followed by gradient salting-out to obtain differential precipitates corresponding to different concentrations of the salting-out agent;
   analyzing to divide the precipitates into ginsenoside $Rg_2$-enriched fractions and ginsenoside $Rg_2$ non-enriched fractions;
   destaining and decolorizing the ginsenoside $Rg_2$-enriched fractions with a destaining agent, followed by concentration to obtain concentrates; and
   adding the lower alcohol to re-crystallize the resulting concentrates, thereby obtaining ginsenoside $Rg_2$.

2. The method according to claim 1, wherein hot-water extraction includes adding the raw material from *Araliaceae panax* to a 16-fold excess of water and heat-extracting for 3 hours, repeatedly, 3 times.

3. The method according to claim 2, wherein the lower alcohol is selected from the group consisting of methyl alcohol, ethyl alcohol, isopropyl alcohol, amyl alcohol and any combination thereof.

4. The method according to claim 3, wherein the salting-out agent is selected from the group consisting of sodium chloride, sodium sulfate, sodium sulfite, ammonium sulfate, other non-toxic inorganic salts and any combination thereof.

5. The method according to claim 4, wherein separating ginsenoside $Rg_2$-enriched fractions and ginsenoside $Rg_2$ non-enriched fractions, from the precipitates, is carried out by thin layer chromatography analysis.

6. The method according to claim 5, wherein the destaining agent is selected from the group consisting of an anion exchange resin, a cation exchange resin, an adsorbent resin and a filler.

7. The method according to claim 6, wherein the recrystallizing comprises a first precipitation and a second precipitation, wherein the first precipitation comprise adding 95% lower alcohol to the ginsenoside $Rg_2$-concentrates, and wherein the second precipitation comprises adding a different concentration of a lower alcohol compared to the first precipitation to obtain respective different crystals compared to the first precipitation.

8. The method according to claim 7, wherein the second precipitating step is carried out by dissolving the first precipitated crystals in 70% alcohol and allowing to stand for 12 hours at room temperature, so as to precipitate isomeric C-20(R) ginsenoside $Rg_2$, adjusting the alcohol concentration of the resulting supernant to 80%, followed by recrystallization at 4° C. for 24 hours to precipitate crystals, adding the resulting crystals to 90% alcohol and heating the mixture to 80° C. so as to dissolve crystals, followed by standing at 10° C. for 24 hours to precipitate mixed-type C-20(SR) ginsenoside $Rg_2$, and allowing the resulting supernant to stand for 12 hours at −20° C., thereby precipitating isomeric C-20(S) ginsenoside $Rg_2$.

* * * * *

UNITED STATES PATENT AND TRADEMARK OFFICE
CERTIFICATE OF CORRECTION

PATENT NO. : 7,884,195 B2
APPLICATION NO. : 11/912804
DATED : February 8, 2011
INVENTOR(S) : Long Yun Li It is certified that error appears in the above-identified patent and that said Letters Patent is hereby corrected as shown below:

On the title page, Item (73), the second Assignee's name is incorrect. Item (73) should read:

-- (73) Assignee: Long Yun Li, Changchun (CN);
Boong-Kyung Ko, Seoul (KR) --

Signed and Sealed this
Twelfth Day of April, 2011

David J. Kappos
*Director of the United States Patent and Trademark Office*